(12) United States Patent
Radu et al.

(10) Patent No.: US 7,575,816 B2
(45) Date of Patent: Aug. 18, 2009

(54) LUMINESCENT LANTHANIDE COMPLEXES WITH IMINE LIGANDS AND DEVICES MADE WITH SUCH COMPLEXES

(75) Inventors: Nora Sabina Radu, Landenberg, PA (US); Daniel David Lecloux, Wilmington, DE (US); Norman Herron, Newark, DE (US); Lucy M. Clarkson, Kennett Square, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 527 days.

(21) Appl. No.: 11/153,108

(22) Filed: Jun. 15, 2005

(65) Prior Publication Data

US 2005/0233232 A1    Oct. 20, 2005

Related U.S. Application Data

(62) Division of application No. 10/195,942, filed on Jul. 15, 2002, now Pat. No. 6,924,047.

(60) Provisional application No. 60/306,395, filed on Jul. 18, 2001.

(51) Int. Cl.
*H01L 51/54* (2006.01)
*H01L 51/46* (2006.01)
*C09K 11/06* (2006.01)
*C07D 213/00* (2006.01)
*C07D 217/00* (2006.01)

(52) U.S. Cl. .................. 428/690; 428/917; 313/504; 313/506; 257/40; 257/E51.044; 136/263; 546/2; 546/10

(58) Field of Classification Search ............. None
See application file for complete search history.

(56) References Cited

U.S. PATENT DOCUMENTS 5,756,224 A * 5/1998 Borner et al. ............... 428/690
2002/0015965 A1 * 2/2002 Sweeting ..................... 435/7.1

FOREIGN PATENT DOCUMENTS

WO    WO 85/01945 A1 *  5/1985
WO    WO 96/20942 A2    7/1996
WO    WO 96/20942 A3    7/1996

OTHER PUBLICATIONS

HCA 104:110945 (for WO 85/01945 A1, May 1985).*
Horrocks, Jr. et al., "Lanthanide Complexes as Nuclear Magnetic Resonance Structural Probes . . . ", Science, vol. 177, pp. 994-996 (Sep. 1972).*
Graddon et al., "Calorimetric Titration Studies of Adduct Formation between Lanthanide beta-Diketonates and Organic Bases in Benzene Solution", J. Chem. Soc., Dalton Trans., Issue 12, pp. 2434-2438 (1981).*
Bourhill et al., "The solid-state photoluminescent quantum yield of triboluminescent materials", Chemical Physics Letters 336 (Aug. 16, 2001), pp. 234-241.*
International Preliminary Examination Report in PCT/US02/22538, Applicant's Docket Reference PE0647PCT, the PCT counterpart of the parent application of the present divisional, now abandoned, Report dated Aug. 04, 2003.

* cited by examiner

*Primary Examiner*—Marie R. Yamnitzky
(74) *Attorney, Agent, or Firm*—John H. Lamming

(57) ABSTRACT

The present invention is generally directed to luminescent lanthanide compounds with imine ligands, and devices that are made with the lanthanide compounds.

11 Claims, 2 Drawing Sheets

US 7,575,816 B2

LUMINESCENT LANTHANIDE COMPLEXES WITH IMINE LIGANDS AND DEVICES MADE WITH SUCH COMPLEXES

RELATED APPLICATIONS

This application is a division of U.S. application Ser. No. 10/195,942 filed Jul. 15, 2002, now U.S. Pat. No. 6,924,047, which claims the benefit of U.S. Provisional Application No. 60/306,395 filed Jul. 18, 2001, the content of which is herein incorporated by reference.

BACKGROUND OF THE INVENTION

1. Field of the Invention

This invention relates to luminescent complexes of lanthanide metals with imine ligands. It also relates to electronic devices in which the active layer includes a lanthanide complex.

2. Description of the Related Art

Luminescent compounds are of interest in a variety of applications, including analytical, bio-analytical and electronic uses. Extensive studies have been made of compounds of the lanthanide metals because of their characteristic sharp emission spectra with very narrow peak-widths. Analytical uses of luminescent complexes of lanthanide metals have been disclosed by, for example, Bell et al. in EP 556 005 and EP 744 451. Electronic devices using luminescent organometallic complexes of lanthanide metals have also been disclosed. In most devices the lanthanide centers are bound to diimine ligands, such as Skotheim et al., U.S. Pat. No. 5,128,587, and Borner et al., U.S. Pat. No. 5,756,224. Heeger et al. have reported devices using europium complexes blended with semiconducting conjugated polymers (*Adv. Mater.* 1999, 11, 1349). Devices containing lanthanide centers bound to phosphineoxide ligands have been disclosed in, for example, Kathirgamanathan et al. WO 98/58037, Wenlian et al. *Journal of the SID* 1998, 6, 133, and Gao et al. *Appl. Phys. Lett.* 1998, 72, 2217.

There is a continuing need for improved luminescent lanthanide compounds. Futhermore, the synthesis and luminescent properties of lanthanide imine compounds have remained largely unexplored.

SUMMARY OF THE INVENTION

The present invention is directed to a luminescent compound comprising a lanthanide metal complexed to at least one imine ligand. It also is directed to an organic electronic device having at least one emitting layer comprising (a) at least one lanthanide compound having at least one imine ligand, and, optionally, (b) a charge transport material. As used herein, the term "imine ligand" is intended to mean a ligand derived from a compound having at least one imine group, —R—N=R—. The imine is selected from a mono-imine having a Formula I, shown in FIG. 1, and a diimine having a Formula II, shown in FIG. 2, where:

in Formulae I and II:
 $R^1$ can be the same or different at each occurrence and is selected from alkyl, fluorinated alkyl, aryl, heteroalkyl, heteroaryl, -$QR^2$, -$QN(R^2)_2$, X, or adjacent $R^1$ groups can join to form 5-membered or 6-membered rings,
 $R^2$ is alkyl or aryl,
 Q is a single bond, alkylene, arylene, or —C(O)—,
 X is Cl, F, Br, or —CN,
 alpha is an integer from 1 to 4;

in Formula II:
 γ is an integer from 1 to 3, and
 δ is 0 or an integer from 1 to 3,
 with the provision that in Formula II there is at least one $R^1$ group that is a fluorinated alkyl or X where X=F.

As used herein, the term "compound" is intended to mean an electrically uncharged substance made up of molecules that further consist of atoms, wherein the atoms cannot be separated by physical means. The term "ligand" is intended to mean a molecule, ion, or atom that is attached to the coordination sphere of a metallic ion. The term "complex", when used as a noun, is intended to mean a compound having at least one metallic ion and at least one ligand. The term "group" is intended to mean a part of a compound, such as a substituent in an organic compound or a ligand in a complex. The term "β-dicarbonyl" is intended to mean a neutral compound in which two ketone groups are present, separated by a CHR group. The term "β-enolate" is intended to mean the anionic form of the β-dicarbonyl in which the H from the CHR group between the two carbonyl groups has been abstracted. The term "charge transport material" is intended to mean material that can receive a charge from an electrode and move it through the thickness of the material with relatively high efficiency and low loss. The phrase "adjacent to," when used to refer to layers in a device, does not necessarily mean that one layer is immediately next to another layer. On the other hand, the phrase "adjacent R groups" is used to refer to R groups that are next to each other in a chemical formula (i.e., R groups that are on atoms joined by a bond). The term "photoactive" refers to any material that exhibits electroluminescence and/or photosensitivity. In addition, the IUPAC numbering system is used throughout, where the groups from the Periodic Table are numbered from left to right as 1-18 (CRC Handbook of Chemistry and Physics, 81$^{st}$ Edition, 2000).

DETAILED DESCRIPTION OF THE PREFERRED EMBODIMENTS

In the lanthanide compounds of the invention, the lanthanide metals are in the +3 oxidation state, and are heptacoordinate or octacoordinate. One or more of the coordination sites are occupied by at least one ligand having one of Formulae I and II. More than one of these ligands, and more than one type of ligand may be coordinated to the metal. Six coordination positions are occupied by β-enolate ligands, and one or two coordination positions are occupied by the monoimine or diimine ligand. The preferred lanthanide metals are Eu, Tb, and Tm. The preferred lanthanide complexes are neutral and non-ionic, and can be sublimed intact.

When the lanthanide compound is applied as a layer by vapor deposition techniques, the ligands are generally chosen so that the final compound is neutral in charge. It is preferred that the additional ligands are β-enolates. More preferred lanthanide compounds are described by one of Formulae III-A, III-B, or IV below:

| | |
|---|---|
| Ln(β-enolate)$_3$(mono-imine)$_1$ | (III-A) |
| Ln(β-enolate)$_3$(mono-imine)$_2$ | (III-B) |
| Ln(β-enolate)$_3$(diimine) | (IV) |

Figure 1:
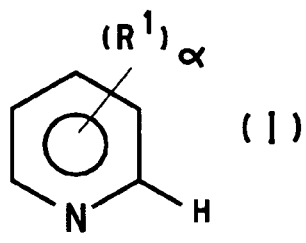
FIG. 1 shows Formula I for a mono-imine ligand useful in the invention.
Figure 2:
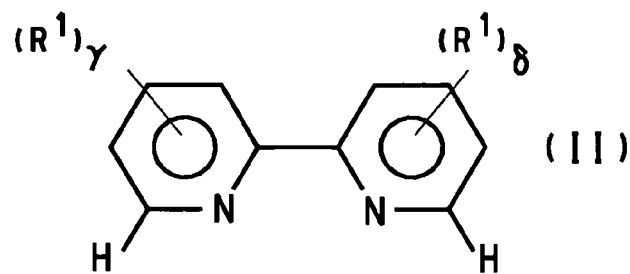
FIG. 2 shows Formula II for a diimine ligand useful in the invention.

Where:
  in Formulae (III-A) and (III-B):
    mono-imine has Formula I of FIG. 1 as described above; and
  in Formula (IV):
    diimine has Formula II of FIG. 2 as described above.

Preferred mono-imine ligands include pyridine ligands (having Formula I) with at least one $R^1$ group including $C_n(H+F)_{2n+1}$, where n is an integer from 1 to 12; —CN; —($C_6H_5$); —($C_4H_3S$); and —($C_4H_3O$).

Examples of suitable mono-imine ligands having Formula I, shown in FIG. 1, include those listed in Table (i) below.

TABLE (i)

| | |
|---|---|
| 3-cyanopyridine | [3-CNpy] |
| 2-dimethylaminopyridine | [2-dmapy] |
| isoquinoline | [isoq] |
| 4-tertbutyl-pyridine | [4-tbpy] |
| 4-phenylpyridine | [4-phpy] |
| 2-(2-thienyl)pyridine | [2-tpy] |
| 4-cyanopyridine | 4-CNpy |

Preferred diimine ligands include bipyridine ligands (having Formula II) with at least one $R^1$ groups are —$C_n(H+F)_{2n+1}$ and —$C_6H_mF_{5-m}$, where m is an integer from 1 to 5.

Examples of suitable diimine ligands having Formula II shown in FIG. 2 include those listed in Tabe (ii) below.

TABLE (ii)

| | |
|---|---|
| 5,5'-bis(trifluoromethyl)-2,2'-bipyridine | [FMbipy] |
| 4,4'-bis(2-trifluoromethylphenyl)-2,2'-bipyridine | [2-FMPbipy] |
| 4,4'-bis(3-trifluoromethylphenyl)-2,2'-bipyridine | [3-FMPbipy] |
| bis(4-fluorophenyl)-2,2'-bipyridine | [FPbipy] |

In some cases, the diimine and mono-imine ligands are commercially available from, for example, Aldrich Chemical Company (Milwaukee, Wis.). "FMbipy" can be prepared according to: Furue, Masaoki; Maruyama, Kazunori; Oguni, Tadayoshi; Naiki, Masahiro; Kamachi, Mikiharu *Inorg Chem*. 1992, 31(18), 3792-5. "2-FMPbipy", "3-FMPbipy", and "FPbipy" can be prepared by Suzuki coupling, according to analogous literature procedures found in: Damrauer, Niels H.; Boussie, Thomas R.; Devenney, Martin; McCusker, James K. *J. Am. Chem. Soc.* 1997, 119(35), 8253-8268.

β-Enolate Ligands

Figure 3:
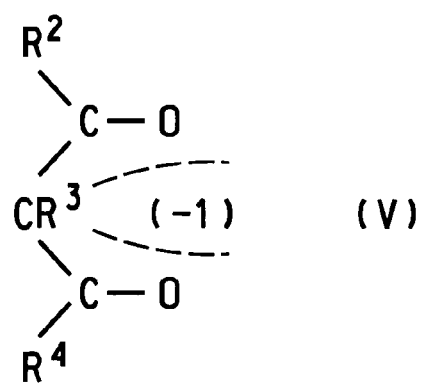
FIG. 3 shows Formula V for the β-enolate ligand useful in the invention.

The β-enolate ligands generally have Formula V shown in FIG. 3, where $R^3$ is the same or different at each occurrence. The $R^3$ groups can be hydrogen, halogen, substituted or unsubstituted alkyl, aryl, alkylaryl or heterocyclic groups. Adjacent $R^3$ groups can be joined to form five- and six-membered rings, which can be substituted. Preferred $R^3$ groups are selected from H, F, $C_n(H+F)_{2n+1}$, —$C_6H_5$, —$C_4H_3S$, and —$C_4H_3O$, where n is an integer from 1 to 12, preferably from 1 to 6.

Examples of suitable β-enolate ligands include but are not limited to the compounds listed in Table (iii) below. The abbreviation for the β-enolate form is given in brackets.

TABLE (iii)

| | |
|---|---|
| 2,4-pentanedionate | [acac] |
| 1,3-diphenyl-1,3-propanedionate | [DI] |
| 2,2,6,6-tetramethyl-3,5-heptanedionate | [TMH] |
| 4,4,4-trifluoro-1-(2-thienyl)-1,3-butanedionate | [TTFA] |
| 7,7-dimethyl-1,1,1,2,2,3,3-heptafluoro-4,6-octanedionate | [FOD] |
| 1,1,1,5,5,5-hexafluoro-2,4-pentanedionate | [F$_6$acac] |
| 1,1,1,3,5,5,5-heptafluoro-2,4-pentanedionate | [F$_7$acac] |
| 1-phenyl-3-methyl-4-i-butyryl-5-pyrazolinonate | PMBP |

The β-dicarbonyls are generally available commercially. 1,1,1,3,5,5,5-heptafluoro-2,4-pentanedionate, $CF_3C(O)CFHC(O)CF_3$, can be prepared using a two-step synthesis, based on the reaction of perfluoropentene-2 with ammonia, followed by a hydrolysis step. This compound should be stored and reacted under anyhydrous conditions as it is susceptible to hydrolysis.

The lanthanide complexes of the invention are made using two routes. The first is by reacting the imine ligand with a Ln(b-enolate)$_3$ complex. Alternatively, these complexes can be obtained by the addition of the b-dicarbonyl and imine compounds to a simple lanthanide metal salt, such as the chloride, nitrate, or acetate. For example, one synthetic method is to dissolve an anhydrous lanthanide acetate, the desired b-dicarbonyl and the imine in dichloromethane. The product can be precipitated by the addition of hexanes. This is particularly useful for forming complexes with heptafluoroacetylacetone. The heptafluoroacetylacetonato lanthanide complexes are generally quite stable to air and moisture.

Examples of lanthanide complexes having Formula III-A or Formula III-B above with imines having Formula I, are given in Table 1 below:

TABLE 1

| Compound | Ln | β-enolate | mono-imine | Formula |
|---|---|---|---|---|
| 1-a | Eu | TTFA | 4-CNpy | III-B |
| 1-b | Eu | TTFA | 2-dmapy | III-A |
| 1-c | Eu | TTFA | isoq | III-B |
| 1-d | Eu | TTFA | 4-tbpy | III-B |
| 1-e | Eu | TTFA | 4-phpy | III-B |
| 1-f | Eu | TTFA | 2-tpy | III-A |
| 1-g | Tb | Acac | 4-CNpy | III-B |
| 1-h | Tb | Acac | 2-dmapy | III-A |
| 1-i | Tb | Acac | isoq | III-B |
| 1-j | Tb | Acac | 4-tbpy | III-B |
| 1-k | Tb | Acac | 4-phpy | III-B |
| 1-l | Tb | Acac | 2-tpy | III-A |

Examples of lanthanide complexes having Formula IV with diimines having Formula II, are given in Table 2 below:

TABLE 2

| Compound | Ln | β-enolate | diimine |
|---|---|---|---|
| 2-a | Eu | Acac | FMbipy |
| 2-b | Eu | Acac | 3-FMPbipy |
| 2-c | Eu | Acac | FPbipy |
| 2-d | Eu | DI | FMbipy |
| 2-e | Eu | DI | 3-FMPbipy |
| 2-f | Eu | DI | FPbipy |
| 2-g | Eu | TMH | FMbipy |
| 2-h | Eu | TMH | 3-FMPbipy |
| 2-i | Eu | TMH | FPbipy |

TABLE 2-continued

| Compound | Ln | β-enolate | diimine |
|---|---|---|---|
| 2-j | Eu | TTFA | FMbipy |
| 2-k | Eu | TTFA | 3-FMPbipy |
| 2-l | Eu | TTFA | FPbipy |
| 2-m | Tb | acac | FMbipy |
| 2-n | Tb | acac | 3-FMPbipy |
| 2-o | Tb | acac | FPbipy |
| 2-p | Tb | DI | FMbipy |
| 2-q | Tb | DI | 3-FMPbipy |
| 2-r | Tb | DI | FPbipy |
| 2-s | Tb | TMH | FMbipy |
| 2-t | Tb | TMH | 3-FMPbipy |
| 2-u | Tb | TMH | FPbipy |
| 2-v | Tm | acac | FMbipy |
| 2-w | Tm | acac | 3-FMPbipy |
| 2-x | Tm | acac | FPbipy |
| 2-y | Tm | TMH | FMbipy |
| 2-z | Tm | TMH | 3-FMPbipy |
| 2-aa | Tm | TMH | FPbipy |

Electronic Device

Figure 4:
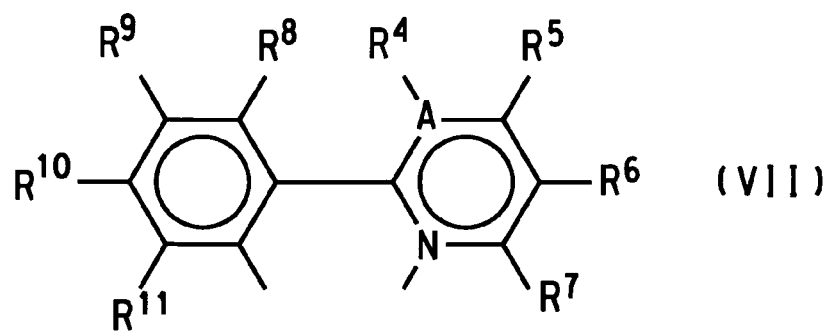
FIG. 4 shows Formula VII for a phenylpyridine ligand.
Figure 5:
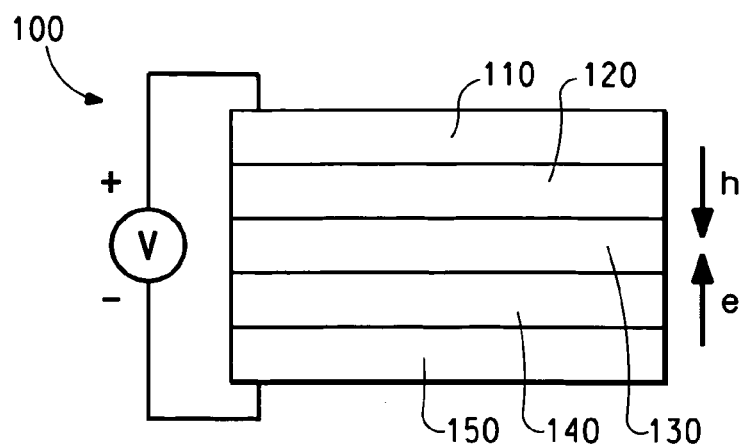
FIG. 5 is a schematic diagram of a light-emitting device (LED).

The present invention also relates to an electronic device comprising at least one photoactive layer positioned between two electrical contact layers, wherein the at least one photoactive layer of the device includes the lanthanide complex of the invention. As shown in FIG. 4, a typical device 100 has an anode layer 110 and a cathode layer 150 and electroactive layers 120, 130 and optionally 140 between the anode 110 and cathode 150. Adjacent to the anode is a hole injection/transport layer 120. Adjacent to the cathode is an optional layer 140 comprising an electron transport material. Between the hole injection/transport layer 120 and the cathode (or optional electron transport layer) is the photoactive layer 130.

Depending upon the application of the device 100, the photoactive layer 130 can be a light-emitting layer that is activated by an applied voltage (such as in a light-emitting diode or light-emitting electrochemical cell), a layer of material that responds to radiant energy and generates a signal with or without an applied bias voltage (such as in a photodetector). Examples of photodetectors include photoconductive cells, photoresistors, photoswitches, phototransistors, and phototubes, and photovoltaic cells, as these terms are describe in Markus, John, *Electronics and Nucleonics Dictionary*, 470 and 476 (McGraw-Hill, Inc. 1966).

The lanthanide complexes of the invention are useful in the photoactive layer 130 of the device. For some lanthanide complexes (such as Tb and Eu), the luminescence spectrum is due to f-f transitions within the metal. Thus, while the intensity of emission can be influenced by the nature of the ligands attached to the lanthanide metal, the wavelength remains relatively constant for all complexes of the same metal. The europium complexes typically have a sharp red emission; the terbium complexes have a sharp green emission. For some lanthanides (such as Tm), the luminescence observed is not due to atomic transitions of the metal. Rather, it is due to either the ligands or the metal-ligand interaction. Under such conditions, the luminescence band can be broad and the wavelength can be sensitive to the ligand used.

While the complexes can be used alone in the light-emitting layer, their emission generally is not strong. It has been found that emission can be greatly improved by combining the lanthanide complexes with materials which facilitate charge transport. The materials can be hole transport materials, electron transport materials or other light-emitting materials which have good transport properties. If the lanthanide complex does not have good hole transport properties, a hole transport material can be co-deposited. Conversely, an electron transport material can be co-deposited if the lanthanide complex does not have good electron transport properties. Some materials can transport both electrons and holes and are more flexible to use.

To achieve a high efficiency LED, the HOMO (highest occupied molecular orbital) of the hole transport material should align with the work function of the anode, the LUMO (lowest un-occupied molecular orbital) of the electron transport material should align with the work function of the cathode. Chemical compatibility and sublimation temp of the materials are also important considerations in selecting the electron and hole transport materials.

It is preferred to use hole transport materials such as N,N'-diphenyl-N,N'-bis(3-methylphenyl)-[1,1'-biphenyl]-4,4'-diamine ("TPD") and bis[4-(N,N-diethylamino)-2-methylphenyl](4-methylphenyl)methane ("MPMP"); electron and hole transporting material such as 4,4'-N,N'-dicarbazole biphenyl ("BCP"); or light-emitting materials with good electron and hole transport properties, such as chelated oxinoid compounds, such as tris(8-hydroxyquinolato)aluminum ("Alq$_3$"), and cyclometalated iridium complexes with 2-phenylpyridines and derivatives.

The iridium complexes have been described in copending application Ser. No. 60/215,362. They can be generally described as compound having Formula VI below:

$$IrL^a_{}L^b_{}L^c_{}L'_{y}L''_{z},\quad \text{(VI)}$$

where:
x=0 or 1, y=0, 1 or 2, and z=0 or 1, with the proviso that:
x=0 or y+z=0 and
when y=2 then z=0;
L'=a bidentate ligand or a monodentate ligand, and is not a phenylpyridine, phenylpyrimidine, or phenylquinoline; with the proviso that:
when L' is a monodentate ligand, y+z=2, and
when L' is a bidentate ligand, z=0;
L''=a monodentate ligand, and is not a phenylpyridine, and phenylpyrimidine, or phenylquinoline; and
$L^a$, $L^b$ and $L^c$ are alike or different from each other and each of $L^a$, $L^b$ and $L^c$ has Formula VII, shown in FIG. 4
wherein:
adjacent pairs of $R^4$-$R^7$ and $R^8$-$R^{11}$ can be joined to form a five- or six-membered ring,
at least one of $R^4$-$R^{11}$ is selected from F, $C_sF_{2s+1}$, $OC_sF_{2s+1}$, and $OCF_2Y$,
s is an integer from 1 to 6,
Y is H, Cl, or Br, and
A is C or N, provided that when A is N, there is no $R^4$.

Preferred iridium compounds include those where $L^a$, $L^b$ and $L^c$ are alike, and either (i) $R^6$ is $CF_3$, $R^{10}$ is F, and all other R are H; or (ii) $R^9$ is $CF_3$ and all other R are H. The iridium complexes above are generally prepared from the appropriate substituted 2-phenylpyridine, phenylpyrimidine, or phenylquinoline. The substituted 2-phenylpyridines, phenylpyrimidines, and phenylquinolines are prepared, in good to excellent yield, using the Suzuki coupling of the substituted 2-chloropyridine, 2-chloropyrimidine or 2-chloroquinoline with arylboronic acid as described in O. Lohse, P. Thevenin, E. Waldvogel *Synlett*, 1999, 45-48. The iridium complex can then be prepared by reacting an excess of the 2-phenylpyridine, phenylpyrimidine, or phenylquinoline, without a solvent, with iridium trichloride hydrate and 3 equivalents of silver trifluoracetate.

When the lanthanide complex is co-deposited with additional charge transport material to form the photoactive layer, the lanthanide complex is generally present in an amount of about up to 85% by volume (15% by volume for the charge transport material) based on the total volume of the emitting layer. Under such conditions the charge transport material is responsible for carrying the electrons and/or holes to the lanthanide. The concentration of the charge transport material has to be above the percolation threshold of approximately 15 volume %, such that a conducting pathway can be established. When the density of the material is close to one, 15 wt % is acceptable as long as the percolation threshold is reached. The lanthanide complex is generally present in an amount of about 0.5 to 75% by weight, based on the total weight of the emitting layer.

In some cases the lanthanide complexes may be present in more than one isomeric form, or mixtures of different complexes may be present. It will be understood that in the above discussion of devices, the term "the lanthanide compound" is intended to encompass mixtures of compounds and/or isomers.

The device generally also includes a support (not shown) which can be adjacent to the anode or the cathode. Most frequently, the support is adjacent the anode. The support can be flexible or rigid, organic or inorganic. Generally, glass or flexible organic films are used as a support. The anode 110 is an electrode that is particularly efficient for injecting or collecting positive charge carriers. The anode is preferably made of materials containing a metal, mixed metal, alloy, metal oxide or mixed-metal oxide. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide, are generally used. The anode 110 may also comprise an organic material such as polyaniline as described in "Flexible light-emitting diodes made from soluble conducting polymers," *Nature* vol. 357, pp 477-479 (11 Jun. 1992).

The anode layer 110 is usually applied by a physical vapor deposition process or spin-cast process. The term "physical vapor deposition" refers to various deposition approaches carried out in vacuo. Thus, for example, physical vapor deposition includes all forms of sputtering, including ion beam sputtering, as well as all forms of vapor deposition such as e-beam evaporation and resistance evaporation. A specific form of physical vapor deposition which is useful is rf magnetron sputtering.

There is generally a hole transport layer 120 adjacent the anode. Examples of hole transport materials for layer 120 have been summarized for example, in Kirk-Othmer Encyclopedia of Chemical Technology, Fourth Edition, Vol. 18, p. 837-860, 1996, by Y. Wang. Both hole transporting molecules and polymers can be used. Commonly used hole transporting molecules, in addition to TPD and MPMP mentioned above, are: 1,1-bis[(di-4-tolylamino)phenyl]cyclohexane (TAPC), N,N'-bis(4-methylphenyl)-N,N'-bis(4-ethylphenyl)-[1,1'-(3, 3'-dimethyl)biphenyl]-4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino) benzaldehyde diphenylhydrazone (DEH), triphenylamine (TPA), 1-phenyl-3-[p-(diethylamino)styryl]-5-[p-(diethylamino)phenyl]pyrazoline (PPR or DEASP), 1,2-trans-bis (9H-carbazol-9-yl)cyclobutane (DCZB), N,N,N',N'-tetrakis (4-methylphenyl)-(1,1'-biphenyl)-4,4'-diamine (TTB), and porphyrinic compounds, such as copper phthalocyanine. Commonly used hole transporting polymers are polyvinylcarbazole, (phenylmethyl)polysilane, poly(3,4-ethylendioxythiophene) (PEDOT), and polyaniline. It is also possible to obtain hole transporting polymers by doping hole transporting molecules such as those mentioned above into polymers such as polystyrene and polycarbonate.

Optional layer 140 can function both to facilitate electron transport, and also serve as a buffer layer or anti-quenching layer to prevent quenching reactions at layer interfaces. Preferably, this layer promotes electron mobility and reduces quenching reactions. Examples of electron transport materials for optional layer 140 include metal chelated oxinoid compounds, such as tris(8-hydroxyquinolato)aluminum ($Alq_3$); phenanthroline-based compounds, such as 2,9-dimethyl-4,7-diphenyl-1,10-phenanthroline (DDPA) or 4,7-diphenyl-1,10-phenanthroline (DPA), and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ).

The cathode 150 is an electrode that is particularly efficient for injecting or collecting electrons or negative charge carriers. The cathode can be any metal or nonmetal having a lower work function than the first electrical contact layer (in this case, an anode). Materials for the second electrical contact layer can be selected from alkali metals of Group 1 (e.g., Li, Cs), the Group 2 (alkaline earth) metals, the Group 12 metals, the lanthanides, and the actinides. Materials such as aluminum, indium, calcium, barium, samarium and magnesium, as well as combinations, can be used.

It is known to have other layers in organic electronic devices. For example, there can be a layer (not shown) between the conductive polymer layer 120 and the active layer 130 to facilitate positive charge transport and/or band-gap matching of the layers, or to function as a protective layer. Similarly, there can be additional layers (not shown) between the active layer 130 and the cathode layer 150 to facilitate negative charge transport and/or band-gap matching between the layers, or to function as a protective layer. Layers that are known in the art can be used. In addition, any of the above-described layers can be made of two or more layers. Alternatively, some or all of inorganic anode layer 110, the conductive polymer layer 120, the active layer 130, and cathode layer 150, may be surface treated to increase charge carrier transport efficiency. The choice of materials for each of the component layers is preferably determined by balancing the goals of providing a device with high device efficiency.

It is understood that each functional layer may be made up of more than one layer.

The device can be prepared by sequentially vapor depositing the individual layers on a suitable substrate. Substrates such as glass and polymeric films can be used. Conventional vapor deposition techniques can be used, such as thermal evaporation, chemical vapor deposition, and the like. Alternatively, the organic layers can be coated from solutions or dispersions in suitable solvents, using any conventional coating technique. In general, the different layers will have the following range of thicknesses: anode 110, 500-5000 Å, preferably 1000-2000 Å; hole transport layer 120, 50-2500 Å, preferably 200-2000 Å; light-emitting layer 130, 10-1000 Å, preferably 100-800 Å; optional electron transport layer 140, 50-1000 Å, preferably 100-800 Å; cathode 150, 200-10,000 Å, preferably 300-5000 Å. The location of the electron-hole recombination zone in the device, and thus the emission spectrum of the device, is affected by the relative thickness of each layer. For example, when an emitter, such as $Alq_3$ is used as the electron transport layer, the electron-hole recombination zone can be in the $Alq_3$ layer. The emission would then be that of $Alq_3$, and not the desired sharp lanthanide emission. Thus the thickness of the electron-transport layer must be chosen so that the electron-hole recombination zone is in the light-emitting layer. The desired ratio of layer thicknesses will depend on the exact nature of the materials used.

It is understood that the efficiency of the devices of the invention made with lanthanide compounds, can be further improved by optimizing the other layers in the device. For example, more efficient cathodes such as Ca, Ba or LiF can be used. Shaped substrates and novel hole transport materials that result in a reduction in operating voltage or increase quantum efficiency are also applicable. Additional layers can also be added to tailor the energy levels of the various layers and facilitate electroluminescence.

EXAMPLES

The following examples illustrate certain features and advantages of the present invention. They are intended to be illustrative of the invention, but not limiting. All percentages are by weight, unless otherwise indicated. Complexes of the type Complexes $(acac)_3Tb(phen)$, $(TTFA)_3Eu(phen)$ and $(TTFA)_3Eu(DPphen)$ were synthesized following procedures known in the art, such as Topilova, Z. M.; Gerasimenko, G. I.; Kudryavtseva, L. S.; Lozinskii, M. O.; Meshkova, S. B. *Russian J. Inorg. Chem.* 1989, 34, 1265.

EXAMPLE 1

Complexes 1-a through 1-l, having the Formulae III-A and III-B were prepared by reacting the corresponding $Ln(\beta\text{-enolate})_3$ with the desired mono-imine in dichloromethane. The products were isolated by filtration.

EXAMPLE 2

$Eu(TMH)_3$(3-FMPbipy). To a $MeOH/CH_2Cl_2$ (3 mL, 1:2 ratio of the two solvents) solution of 3-FMPbipy (0.148 g, 0.33 mmol) was added $Eu(TMH)_3$ (0.234 g, 0.33 mmol) dissolved in MeOH (2 mL). The resulting solution was stirred at room temperature for 48 hours. After the solvent was evaporated the white solid was washed with hexane to yield the product 14% yield (0.050 g). $^{19}F\{^1H\}$ NMR ($CD_2Cl_2$, 376 MHz) $\delta$ is –63.36.

EXAMPLE 3

$Eu(TMH)_3$(Fpbipy). To a $MeOH/CH_2Cl_2$ (3 mL, 1:2 ratio of the two solvents) solution of Fpbipy (0.187 g, 0.27 mmol) was added $Eu(TMH)_3$ (0.187 g, 0.27 mmol) dissolved in MeOH (2 mL). The resulting solution was stirred at room temperature for 48 hours. After the solvent was evaporated the white solid was washed with hexane to yield the product 70% yield (0.138 g).

Other complexes in Table 2 above were prepared in an analogous manner.

EXAMPLE 4

This example illustrates the formation of OLEDs using the lanthanide complexes of the invention.

Thin film OLED devices including a hole transport layer (HT layer), electroluminescent layer (EL layer) and an electron transport layer (ET layer) were fabricated by the thermal evaporation technique. An Edward Auto 306 evaporator with oil diffusion pump was used. The base vacuum for all of the thin film deposition was in the range of $10^{-6}$ torr. The deposition chamber was capable of depositing five different films without the need to break up the vacuum.

An indium tin oxide (ITO) coated glass substrate was used, having an ITO layer of about 1000-2000 Å. The substrate was first patterned by etching away the unwanted ITO area with 1N HCl solution, to form a first electrode pattern. Polyimide tape was used as the mask. The patterned ITO substrate was then cleaned ultrasonically in aqueous detergent solution. The substrate was then rinsed with distilled water, followed by isopropanol, and then degreased in toluene vapor for about 3 hours.

The cleaned, patterned ITO substrate was then loaded into the vacuum chamber and the chamber was pumped down to $10^{-6}$ torr. The substrate was then further cleaned using an oxygen plasma for about 5-10 minutes. After cleaning, multiple layers of thin films for the HT, EL and ET layers were then deposited sequentially onto the substrate by thermal evaporation. Finally, patterned metal electrodes of Al were deposited through a mask, with a thickness in the range of 700-760 Å. The thicknesses of the films were measured during deposition using a quartz crystal monitor (Sycon STC-200). The reported film thicknesses are nominal, calculated assuming the density of the material deposited to be one. The completed OLED device was then taken out of the vacuum chamber and characterized immediately without encapsulation. A summary of the device layers and thicknesses is given in Table 3, below.

Figure 6:
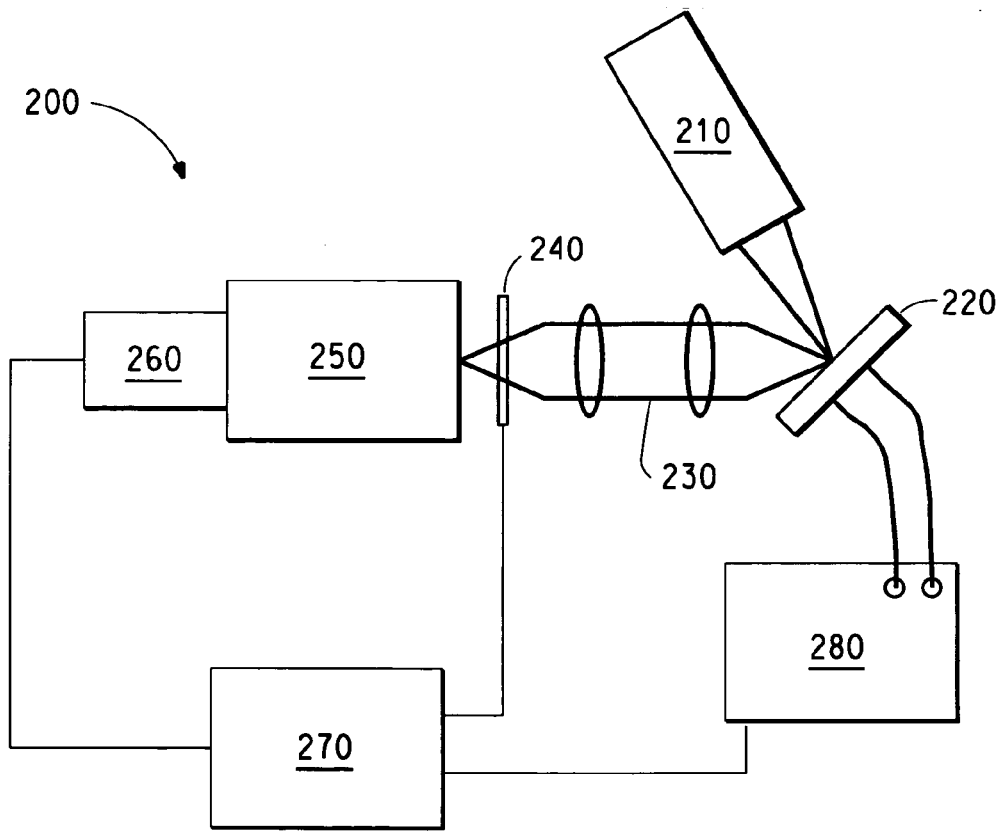
FIG. 6 is a schematic diagram of an LED testing apparatus.

The OLED samples were characterized by measuring the (1) current-voltage (I-V) curves, (2) electroluminescence radiance versus voltage, and (3) electroluminescence spectrum versus voltage. The apparatus used, 200, is shown in FIG. 6. The I-V curves of an OLED sample, 220, were measured with a Keithley Source-Measurement Unit Model 237, 280. The electroluminescence radiance (in the unit of $cd/m^2$) vs. voltage was measured with a Minolta LS-110 luminescence meter, 210, while the voltage was scanned using the Keithley SMU. The electroluminescence spectrum were obtained by collecting light using a pair of lenses, 230, through an electronic shutter, 240, dispersed through a spectrograph, 250, and then measured with a diode array detector, 260. All three measurements were performed at the same time and controlled by a computer, 270. The efficiency of the device at certain voltage was determined by dividing the electroluminescence radiance of the LED by the current density needed to run the device. The unit of measurement is Cd/A. The results are given in Table 3 below.

TABLE 3

| Sample | HT layer Thickness, Å | EL layer thickness, Å | ET layer thickness, Å | Peak Radiance, $cd/m^2$ | Peak efficiency, cd/A | Approximate Peak Wavelengths, nm |
|---|---|---|---|---|---|---|
| 1 | MPMP 508 | Example 2, 425 | DDPA, 420 | 8 | 0.25 | 617 |

TABLE 3-continued

| Sample | HT layer Thickness, Å | EL layer thickness, Å | ET layer thickness, Å | Peak Radiance, cd/m² | Peak efficiency, cd/A | Approximate Peak Wavelengths, nm |
|---|---|---|---|---|---|---|
| 2 | MPMP 535 | Example 3, 441 | DDPA, 403 | 2.5 | 0.16 | 617 |

DDPA = 2,9-dimethyl-4,7-diphenyl-1,10-phenanthroline
ET = electron transport
HT = hole transport
MPMP = bis[4-(N,N-diethylamino)-2-methylphenyl](4-methylphenyl)methane

What is claimed is:

1. A lanthanide compound having Formula III-B below:

Ln(β-enolate)₃(mono-imine)₂ (III-B)

wherein the mono-imine is selected from 3-cyanopyridine; 2-dimethylaminopyridine; isoquinoline; 4-tertbutyl-pyridine; 4-phenylpyridine; and 2-(2-thienyl)pyridine.

2. The compound of claim 1 wherein Ln is selected from Eu, Tb and Tm.

3. The compound of claim 1 wherein the β-enolate is selected from 2,4-pentanedionate; 1,3-diphenyl- 1,3-propanedionate; 2,2,6,6-tetramethyl-3,5-heptanedionate; 4,4,4-trifluoro-1-(2-thienyl)-1,3-butanedionate; 7,7-dimethyl-1,1,1,2,2,3,3-heptafluoro-4,6-octanedionate; 1,1,1,5,5,5-hexaflouro-2,4-pentanedionate; 1-phenyl-3-methyl-4-i-butyryl-pyrazolinonate; and 1,1,1,3,5,5,5-heptafluoro-2,4-pentanedionate.

4. An electronic device comprising a photoactive layer, wherein the photoactive layer comprises the lanthanide compound of claim 1.

5. The device of claim 4 wherein the lanthanide compound is present in an amount of up to about 85% by volume based on the total volume of the photoactive layer.

6. The device of claim 4 wherein the photoactive layer further comprises (b) a charge transport material.

7. The device of claim 6 wherein the charge transport material (b) is a hole transport material selected from N,N'-diphenyl-N,N'-bis(3 -methylphenyl)-[1,1'-biphenyl]-4,4'-diamine and bis[4-(N,N-diethylamino)-2-methylphenyl](4-methylphenyl)methane.

8. The device of claim 6 wherein the charge transport material (b) is an electron and hole transporting material selected from 4,4'-N,N'-dicarbazole biphenyl; chelated oxinoid compounds of aluminum; and cyclometalated iridium complexes with 2-phenylpyridines.

9. The device of claim 4, further comprising a hole transport layer, wherein the hole transport layer comprises a hole transport material selected from N,N'-diphenyl-N,N'-bis(3 -methylphenyl)-[1,1'-biphenyl]-4,4'-diamine; 1,1-bis[(di-4-tolylamino) phenyl]cyclohexane; N,N'-bis(4-methylphenyl)-N,N'-bis(4-ethylphenyl)-[1,1'-(3,3'-dimethyl)biphenyl]-4,4'-diamine; tetrakis-(3-methylphenyl)-N,N,N',N'-2,5-phenylenediamine; α-phenyl-4-N,N-diphenylaminostyrene; p-(diethylamino)benzaldehyde diphenylhydrazone; triphenylamine; bis[4-(N,N-diethylamino)-2-methylphenyl](4-methylphenyl)methane; 1-phenyl-3-[p-(diethylamino)styryl]-5-[p-(diethylamino)phenyl] pyrazoline; 1,2-trans-bis (9H-carbazol-9-yl)cyclobutane; N,N,N',N'-tetrakis(4-methylphenyl)-(1,1'-biphenyl)-4,4'-diamine; porphyrinic compounds; and combinations thereof.

10. The device of claim 4, further comprising an electron transport layer, wherein the electron transport layer comprises an electron transport material selected from tris(8-hydroxyquinolato)aluminum; 2,9-dimethyl-4,7-diphenyl-1,10-phenanthroline; 4,7-diphenyl- 1,10-phenanthroline; 2-(4-biphenylyl)-5 -(4-t-butylphenyl)- 1,3,4-oxadiazole; 3-(4-biphenylyl)-4-phenyl-5-(4-t-butylphenyl)-1,2,4-triazole; and combinations thereof.

11. A lanthanide compound having Formula III-B

Ln(β-enolate)₃(mono-imine)₂ (III-B)

and having a structure selected from compounds as provided in the below table,

TABLE 1

| Compound | Ln | β-enolate | mono-imine | Formula |
|---|---|---|---|---|
| 1-a | Eu | TTFA | 4-CNpy | III-B |
| 1-c | Eu | TTFA | isoq | III-B |
| 1-d | Eu | TTFA | 4-tbpy | III-B |
| 1-e | Eu | TTFA | 4-phpy | III-B |
| 1-g | Tb | Acac | 4-CNpy | III-B |
| 1-i | Tb | Acac | isoq | III-B |
| 1-j | Tb | Acac | 4-tbpy | III-B |
| 1-k | Tb | Acac | 4-phpy | III-B | wherein TTFA is 4,4,4-trifluoro-1-(2-thienyl)-1,3-butanedionate; Acac is 2,4-pentanedionate; 4-CNpy is 4-cyanopyridine; isoq is isoquinoline; 4-tbpy is 4-tertbutyl-pyridine; and 4-phpy is 4-phenylpyridine.

* * * * *

UNITED STATES PATENT AND TRADEMARK OFFICE
CERTIFICATE OF CORRECTION

PATENT NO. : 7,575,816 B2
APPLICATION NO. : 11/153108
DATED : August 18, 2009
INVENTOR(S) : Radu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 772 days.

Signed and Sealed this

Seventh Day of September, 2010

David J. Kappos
*Director of the United States Patent and Trademark Office*